(12) United States Patent
Aichinger et al.

(10) Patent No.: US 6,504,056 B2
(45) Date of Patent: Jan. 7, 2003

(54) TRANSPORT AND/OR STORAGE OF ACRYLIC ACID

(75) Inventors: Heinrich Aichinger, Mannheim (DE); Gerhard Nestler, Ludwigshafen (DE); Paul Leon Kageler, Lake Jackson, TX (US)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/845,268

(22) Filed: May 1, 2001

(65) Prior Publication Data

US 2002/0165410 A1 Nov. 7, 2002

(51) Int. Cl.⁷ ............... C07C 51/42; C07C 57/02
(52) U.S. Cl. ............ 562/600; 562/600; 562/598
(58) Field of Search ................. 562/600, 598

(56) References Cited

U.S. PATENT DOCUMENTS

| | | | |
|---|---|---|---|
| 2,978,501 A | 4/1961 | Adams | |
| 5,130,471 A | 7/1992 | Heiman et al. | |
| 5,221,764 A | 6/1993 | Roling | |
| 6,046,357 A | * | 4/2000 | Levy et al. |

FOREIGN PATENT DOCUMENTS

| | | |
|---|---|---|
| EP | 0 178 168 | 4/1986 |
| EP | 0 467 851 | 1/1992 |
| EP | 0 620 206 | 10/1994 |
| EP | 0 685 447 | 12/1995 |
| EP | 0 765 856 | 4/1997 |

OTHER PUBLICATIONS

European Basic Acrylic Monomer Manufacturers Association, Pages 7 and 8, "Safe Handling and Storage of Acrylic Acid", 1996.

* cited by examiner

Primary Examiner—Sreeni Padmanabhan
Assistant Examiner—Farhad Forohar
(74) Attorney, Agent, or Firm—Oblon, Spivak, McClelland, Maier & Neustadt, P.C.

(57) ABSTRACT

A method of transporting and/or storing pure acrylic acid comprises ensuring by means of appropriate measures that the pure acrylic acid is partly crystalline during the entire duration of transport and/or storage.

20 Claims, No Drawings

TRANSPORT AND/OR STORAGE OF ACRYLIC ACID

FIELD OF THE INVENTION

The invention relates to a method of transporting and/or storing stabilized pure acrylic acid.

Acrylic acid is used either as such or in the form of its salts or esters for preparing polymers whose most important fields of application are, for example, adhesives, superabsorbents or binders.

BACKGROUND OF THE INVENTION

Acrylic acid is generally produced industrially by catalytic gas-phase oxidation of propane, propene and/or acrolein. In such a process, the starting materials, generally diluted with inert gases such as nitrogen, carbon dioxide and/or steam, are passed in admixture with oxygen over mixed transition metal oxide catalysts at elevated temperatures and atmospheric or superatmospheric pressure and are oxidized to form a product gas mixture comprising acrylic acid.

A basic separation of the acrylic acid from the product gas stream is carried out by fractional condensation of the product gas mixture or by absorption in a suitable absorption medium, for example water or a high-boiling inert solvent, for example a mixture of from 70 to 75% by weight of diphenyl ether and from 25 to 30% by weight of biphenyl.

Removal of the absorption medium by extraction and/or distillation, for example removal of the absorption medium water by distillation, azeotropic distillation and/or extraction of the acid from the aqueous solution and subsequent removal of the extractant by distillation, and/or application of other separation steps, for example crystallization, generally gives an acrylic acid which for the purposes of the present invention will be referred to as crude acrylic acid.

Crude acrylic acid is not a pure product but contains many impurities typical of the gas-phase catalytic oxidative production route. These are, in particular, acetic acid, propionic acid, water and low molecular weight aldehydes such as acrolein, methacrolein, propionaldehyde, n-butyraldehyde, benzaldehyde, furfurals and crotonaldehyde.

Further undesirable by-products which accompany acrylic acid in the condensed phase are the acrylic acid oligomers formed by Michael addition of acrylic acid onto itself or onto the acrylic acid dimer formed in this way, known as Michael adducts. For statistical reasons, the formation of diacrylic acid predominates.

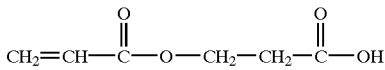

If such a crude acrylic acid were to be used directly as monomer in free-radical polymerizations, impurities incapable of free-radical polymerization present in the crude acrylic acid, for example acetic acid or propionic acid, would remain as volatile compounds in the polymerization product, which would lead, in particular, to undesirable odor in the product. Furthermore, such aldehyde impurities are, in particular, disadvantageous in that they influence the induction time of free-radical polymerizations, i.e. the time between the attainment of the polymerization temperature and the actual commencement of the polymerization. In addition, they generally influence the degree of polymerization and can lead to discoloration in the polymers.

A particularly critical impurity in crude acrylic acid is diacrylic acid. Diacrylic acid reacts with monomeric acrylic acid much more slowly in free-radical polymerization and therefore remains either as such or in copolymerized form in the polymerization product. On subsequent thermal treatment, this leads to formation of monomeric acrylic acid, which is generally undesirable. This is particularly problematical when polymeric acrylic acid is used in superabsorbents, a main application area for it.

The specification limits for maximum tolerable contents of impurities are therefore narrow for polymerization grade acrylic acid. The impurities mentioned therefore have to be very largely removed from the crude acrylic acid, for example by rectification and/or crystallization.

In this way, it is possible to obtain acrylic acid whose purity is $\geq 99\%$ by weight, based on the sum of all constituents present, including the polymerization inhibitor added to prevent undesirable premature free-radical polymerization of the acrylic acid. Acrylic acids having a purity, i.e. an acrylic acid content, of $\geq 99\%$ by weight, balance impurities, are for the purposes of the present invention collectively referred to as "pure acrylic acid".

Thus, for the purposes of the present invention, pure acrylic acids are, in particular, acrylic acids whose purity, as indicated above, based on the sum of all constituents present is $\geq 99\%$ by weight, or $\geq 99.5\%$ by weight, or $\geq 99.75\%$ by weight or $\geq 99.9\%$ by weight.

Pure acrylic acid is frequently produced by direct further processing of freshly prepared crude acrylic acid, i.e. the product mixture from the catalytic gas-phase oxidation of propene, propane or acrolein, because virtually no acrylic acid oligomers have yet formed in this. Likewise, pure acrylic acid is generally used shortly after it has been produced.

However, in some cases it can be necessary to store pure acrylic acid for prolonged periods of time and/or to transport it over relatively long distances. This results in a deterioration in the quality of the pure acrylic acid, since increased, undesirable formation of diacrylic acid is essentially unavoidable during storage and/or transport.

From the Technical Information leaflet TI/ED 1330 d (June 1992) of BASF Aktiengesellschaft it is known that diacrylic acid formation in pure acrylic acid is promoted by a relatively high storage temperature and by the presence of water. In this Technical Information leaflet, it is also stated that the formation of diacrylic acid occurring in pure acrylic acid cannot be prevented by means of chemical additives and that diacrylic acid formation in pure acrylic acid containing less than 0.1% by weight of water is about 0.5–1% by weight per month, based on the acrylic acid content.

Thus, according to the above information, the only ways of limiting diacrylic acid formation in pure acrylic acid are to store and/or transport the pure acrylic acid in the presence of as little water as possible and at a temperature which is as low as possible. Disadvantages are the formation of crystals and the problems associated with melting these. According to DE-A 199 23 389, the addition of water decreases the rate of diacrylic acid formation compared to water-free pure acrylic acid, accompanied by a pronounced lowering of the freezing point. Since the solidification point decreases as the water content increases, aqueous pure acrylic acid can be cooled to a lower temperature and the formation of diacrylic acid can be largely suppressed. However, a disadvantage of the abovementioned method is that, for the same quantities of pure acrylic acid, the transport and/or storage capacity has to be increased to an extent corresponding to the amount of water added.

In addition, with regard to the abovementioned publication, a certain safety margin to the solidification point of acrylic acid should always be maintained, for the following reasons:

According to Ullmanns Encyclopädie der technischen Chemie, 4th edition, Volume 7 (1994), Verlag Chemie, page 85, column 2, the thawing of frozen pure acrylic acid requires extreme care, because pure acrylic acid becomes locally depleted in polymerization inhibitor on freezing (it is this phase separation on which the utility of fractional crystallization as a purification method is based) and unstabilized acrylic acid can polymerize explosively with great evolution of heat. This applies particularly when use is made of polymerization inhibitors which are only fully effective in the presence of molecular oxygen (for example, hydroquinone monomethyl ether and/or monoethyl ether), because the crystallization process is also accompanied by the stabilizing dissolved oxygen being severely depleted locally in the acrylic acid. In these cases, the frozen pure acrylic acid must, for safety reasons, be mixed from time to time in the presence of air during melting so as to bring about uniform saturation with oxygen as soon as possible. Furthermore, the external heat source used for thawing must not, for safety reasons, have an excessively high temperature, which is why thawing takes a comparatively long time during which undesirable diacrylic acid formation once again takes place.

For these reasons, the storage and/or transport of pure acrylic acid in the industry has hitherto been carried out at $\geq 15°$ C. In the technical information pamphlet of the EBAM (European Basic Acrylic Monomer Manufacturers Association) "SAFE HANDLING AND STORAGE OF ACRYLIC ACID", 1996, pages 7 and 8, it is stated that it is of great importance to avoid freezing of acrylic acid during transport and/or storage. A storage temperature for acrylic acid in the range from 15 to 25° C. is recommended. This means that a safety margin of at least 2° C. to the solidification point of acrylic acid would normally be maintained, since fluctuations in the effectiveness of the temperature control facility employed cannot be completely ruled out.

However, a disadvantage of this method is that, according to our own studies on pure acrylic acid having a purity of $\geq 99.8\%$ by weight and a water content of $\geq 0.05\%$ by weight, the rate of diacrylic acid formation at 15° C. is still 40 ppm by weight per day (at a pressure of 1 atm; this boundary condition always applies in the present text unless a different pressure is expressly specified) and, furthermore, the safety margin maintained of 2° C. is comparatively small.

SUMMARY OF THE INVENTION

It is an object of the present invention to provide an improved method of transporting and/or storing pure acrylic acid which does not have the disadvantages of the prior art. In particular, diacrylic acid formation should be largely suppressed, the method should be simple and economical and should meet high safety standards, in particular during emptying of the transport and/or storage container.

We have found that this object is achieved by a method of transporting and/or storing pure acrylic acid which comprises ensuring by means of appropriate measures that the pure acrylic acid is partly crystalline during the entire duration of transport and/or storage.

It has surprisingly been found that pure acrylic acid can be transported and/or stored at its solidification point or at temperatures below its solidification point since simple and hazard-free melting is always possible as long as the pure acrylic acid is in a partly crystalline state during the entire duration of transport and/or storage. In addition, this largely suppresses undesirable diacrylic acid formation.

Partly crystalline pure acrylic acid is a pure acrylic acid in which liquid and solid phases are always simultaneously present. A thermodynamic equilibrium is established between the solid phase and the liquid phase, and this is characterized by a constant equilibrium temperature over the entire period in which the partly crystalline state is maintained. Since pure acrylic acid contains, as indicated above, a certain proportion of up to 1% by weight of impurities, the equilibrium temperature has a value in the range from 10 to 15° C., in particular from 12 to 14° C., depending on the proportion of impurities in the particular pure acrylic acid.

Pure acrylic acid always, in the present method too, has to be admixed with polymerization inhibitors for stabilization unless it is used for polymerization immediately after it has been produced.

DETAILED DESCRIPTION OF THE INVENTION

Polymerization inhibitors which can be used are in principle all known acrylic acid polymerization inhibitors. They are preferably soluble in pure acrylic acid in the amount to be used. The amount used is, based on the amount of acrylic acid, generally $\leq 1000$ ppm by weight. In the method of the present invention, the polymerization inhibitor content is typically $\geq 10$ ppm by weight (again based on the amount of acrylic acid).

Typical polymerization inhibitor contents are from 50 to 750 ppm by weight, or from 75 to 500 ppm by weight or from 100 to 400 ppm by weight or from 100 to 300 ppm by weight. Examples of polymerization inhibitors that can be used according to the present invention are those described in EP-A 765 856, EP-A 685 447, EP-A 620 206, EP-A 467851, EP-A 178168, WO 92/1665, DE-A 1618141, DE-PC 1543996, DE-A 2931553, U.S. Pat. Nos. 5,221,764, 5,130,471 and 2,978,501. The polymerization inhibitors described in the abovementioned publications can in each case be used as such or in the combinations recommended in these publications. The polymerization inhibitors described in WO 99/21893 are also suitable for the purposes of the present invention, either as such or in the combinations recommended there.

Examples of these polymerization inhibitors are molecular oxygen, phenothiazines, phenol compounds, N-oxyl radicals, nitroso compounds and p-phenylenediamines. Suitable individual representatives of these groups are phenothiazine, hydroquinone, the monomethyl ether of hydroquinone, the monoethyl ether of hydroquinone, 4-hydroxy-2,2,6,6-tetramethyl-1-oxylpiperidine, benzoquinone, 4-nitrosophenol and p-phenylenediamine.

In the method of the present invention, it is advantageous to use only hydroquinone or only the monomethyl ether of hydroquinone or only the monoethyl ether of hydroquinone or mixtures of two or all three of these hydroquinone compounds as polymerization inhibitors. As regards the amounts used, what has been said above applies. This means that they are generally used in amounts of $\leq 5000$ ppm by weight, or $\leq 2000$ ppm by weight, usually $\leq 1000$ ppm by weight, frequently $\leq 500$ ppm by weight, often $\leq 300$ ppm by weight, sometimes $\leq 200$ ppm by weight, but generally $\geq 10$ ppm by weight, usually $\geq 50$ ppm by weight, based on the amount of acrylic acid present in the pure acrylic acid.

The amounts of other polymerization inhibitors present in the pure acrylic acids to be treated according to the present invention is at the same time, likewise based on the acrylic acid content, a total of ≦20 ppm by weight, or ≦10 ppm by weight or ≦5 ppm by weight and particularly advantageously ≦2 ppm by weight or ≦1 ppm by weight. The abovementioned values also apply, in particular, to an individual content of phenothiazine.

The method of the present invention is particularly useful when the storage and/or transport time is at least 1 day, or at least 2 days or at least 3 days or at least 4 days or at least 5 days or at least 6 days or at least 7 days. It can, however, also be ≧10 days, or ≧20 days or ≧30 days or ≧40 days or ≧50 days. The storage and/or transport time in the method of the present invention is advantageously ≦6 months, frequently ≦5 months, often ≦4 months, usually ≦3 months and frequently ≦2 months or ≦1 month.

The diacrylic acid content of the pure acrylic acid to be stored according to the present invention is, based on the acrylic acid content, ≦10,000 ppm by weight. The diacrylic acid content on the above basis is usually ≦8000 ppm by weight, frequently ≦6000 ppm by weight or ≦4000 ppm by weight.

However, the method of the present invention is, in particular, also applicable to pure acrylic acids whose diacrylic acid content based on the acrylic acid content is ≦3000 ppm by weight, or ≦2000 ppm by weight or ≦1500 ppm by weight or ≦1000 ppm by weight, or else ≦750 ppm by weight or ≦500 ppm by weight, frequently ≦250 ppm by weight or ≦100 ppm by weight or ≦50 ppm by weight or ≦25 ppm by weight.

The aldehyde content of the pure acrylic acids to be stored and/or transported, based on their acrylic acid content, is likewise ≦10,000 ppm by weight, usually ≦750 ppm by weight or ≦500 ppm by weight, frequently ≦250 ppm by weight of ≦100 ppm by weight or ≦50 ppm by weight or ≦25 ppm by weight. Of course, the aldehyde content on the above basis of the pure acrylic acids to be treated according to the present invention can also be ≦20 ppm by weight, or ≦15 ppm by weight, or else ≦10 ppm by weight or ≦5 ppm by weight, or ≦1 ppm by weight or ≦0.5 ppm by weight or ≦0.1 ppm by weight.

The method of the present invention can, however, also be applied to pure acrylic acids whose total content of acetic acid and propionic acid, based on the acrylic acid present, is ≦10,000 ppm by weight, frequently ≦8000 ppm by weight, often ≦6000 ppm by weight, or ≦4000 ppm by weight, or ≦3000 ppm by weight or ≦2000 ppm by weight or ≦1000 ppm by weight or ≦100 ppm by weight.

The method of the present invention is thus applicable, in particular, to pure acrylic acid having the following contents (based on its total weight):

a) content of acrylic acid ≧99% by weight, content of diacrylic acid ≦2000 ppm by weight, content of aldehydes ≦10 ppm by weight, content of monomethyl ether of hydroquinone (MEHQ) and monoethyl ether of hydroquinone (EEHQ) together ≦1000 ppm by weight and ≧20 ppm by weight, content of phenothiazine ≦5 ppm by weight and content of acetic acid and propionic acid together ≦3000 ppm by weight; or b) content of acrylic acid ≧99.5% by weight, content of diacrylic acid ≦1000 ppm by weight, content of aldehydes ≦5 ppm by weight, content of MEHQ and EEHQ together ≦500 ppm by weight and ≧20 ppm by weight, content of phenothiazine ≦3 ppm by weight and content of acetic acid and propionic acid together ≦2000 ppm by weight; or c) content of acrylic acid ≧99.8% by weight, content of diacrylic acid ≦1000 ppm by weight, content of aldehydes ≦1 ppm by weight, content of MEHQ and EEHQ together ≦250 ppm by weight and ≧20 ppm by weight, content of phenothiazine ≦1 ppm by weight and content of acetic acid and propionic acid together ≦1500 ppm by weight; or d) content of acrylic acid ≧99.8% by weight, content of diacrylic acid ≦500 ppm by weight, content of aldehydes: per aldehyde, ≦1 ppm by weight, content of MEHQ=100 to 300 ppm by weight, content of phenothiazine ≦1 ppm by weight and content of acetic acid and propionic acid together ≦1000 ppm by weight.

Acrylic acid is always stored and transported in insulated containers. Insulation by means of polyurethane foam, for example, can be sufficient for this purpose, but the transport and/or storage containers are frequently provided with at least one heat exchanger, for example a double wall which wholly or partly surrounds the container and/or internal cooling coils. Heat exchange media, i.e. heating and/or cooling media, can be passed through these heat exchangers. Preferred cooling media for the present method are brine, water or water/alkanol mixtures, in particular methanol, ethanol or ethylene glycol.

The temperature of the cooling medium is generally in the range from −20 to +10° C., in particular from −10 to +10° C.

According to the present invention, the pure acrylic acid which has been introduced in liquid form into the transport and/or storage container is cooled or allowed to cool until a proportion of from 10 to 90%, based on the total amount of pure acrylic acid in the transport and/or storage container, preferably a proportion of from 20 to 70% on the same basis, has been frozen.

For this purpose, a cooling medium can be introduced into the heat exchanger or exchangers of the transport and/or storage tank.

Under some weather conditions, namely at low outdoor temperatures, in particular below 0° C., preferably below −10° C., an increasing proportion of the initially liquid pure acrylic acid freezes as the duration of transport and/or storage increases, due to the effect of the exterior temperature alone. Thus, for example, it has been found that in the case of transport containers having a capacity of 20 metric tons whose entire outer surface has been insulated with a 50 mm thick layer of polyurethane foam, the freezing point of pure acrylic acid is reached in the transport container after from about 7 to 8 days at an exterior temperature of 0° C., but after only 5 days at an exterior temperature of −10° C., in each case with the transport containers having been loaded with liquid acrylic acid at 25° C. After the freezing point has been reached, the process of crystallization of the acrylic acid proceeds from the outside inward, but only very slowly because of the comparatively high crystallization energy of 154 MJ per metric ton and the increasingly thick and insulating layer of crystallized acrylic acid on the interior wall of the container. For this reason, if a 20 metric ton transport and/or storage container provided with the above-described insulation is filled with liquid acrylic acid at 25° C., limiting the transport and/or storage time to not more than 10 days can ensure, for example at an external temperature of 0° C., that the pure acrylic acid is always partly crystalline.

The critical step during the transport and/or storage of pure acrylic acid, namely the emptying of the transport and/or storage container, can be carried out safely as long as the essential condition according to the present invention, namely that the pure acrylic acid is always in partly crystalline form, is adhered to.

The emptying of the transport and/or storage container requires melting of the partly crystalline, i.e. partly frozen, pure acrylic acid present therein. For this purpose, if the transport and/or storage container is equipped with at least one heat exchanger, in particular a double wall, a heating medium can be introduced into at least one heat exchanger. However, to avoid the known risks of sometimes explosive polymerization and diacrylic acid formation, the temperature of the heating medium has to be kept at or below 40° C. The preferred heating medium is warm water. The use of warm water heating at a maximum temperature of 40° C. is safe, but slow because of the small temperature gradient. However, a problem is that the crystals which have been greatly depleted in polymerization inhibitor can polymerize during melting. Better heat transfer is achieved when the partly crystalline and partly liquid acrylic acid in the transport and/or storage container is melted by taking liquid acrylic acid containing polymerization inhibitor from the transport and/or storage container, heating it to a temperature in the range from 15 to 40° C. in an external heat exchanger and subsequently recirculating it to the transport and/or storage container until the entire contents of the transport and/or storage container have been completely melted. Here, liquid acrylic acid is taken from the transport and/or storage container and heated liquid acrylic acid is at the same time returned to the transport and/or storage container.

It has been found that the polymerization inhibitor which is present in the liquid acrylic acid and has had to be added to the pure acrylic acid anyway for the purposes of transport and/or storage is sufficient for the solid pure acrylic acid still present in the transport and/or storage container, which acid is, as is known, depleted in polymerization inhibitor, to be able to be melted safely by means of the pure acrylic acid which has been taken from the transport and/or storage container and heated. The addition of further amounts of polymerization inhibitor for the purposes of melting, which would at the same time represent further contamination of the pure acrylic acid, is not necessary according to the method of the present invention.

The withdrawal of the liquid pure acrylic acid from the transport and/or storage container and the return of this after heating are carried out in a manner known to those skilled in the art. The withdrawal is preferably carried out by means of a tube which dips into the liquid pure acrylic acid and has, in particular, lateral perforations having a diameter smaller than the internal diameter of the tube. The connecting line between the offtake point of the liquid pure acrylic acid, the transport and/or storage container and the external heat exchanger and also the return line for the heated acrylic acid to the transport and/or storage container are advantageously thermally insulated.

The liquid heated pure acrylic acid is particularly preferably returned to the transport and/or storage container via a spray device by means of which improved mixing and thus melting of the frozen material is achieved.

If an appropriate, thermostatable reservoir is available, the pure acrylic acid taken off in liquid form from the transport and/or storage container can be conveyed into this reservoir and after heating therein can be returned to the transport and/or storage container for the purpose of melting the partly crystalline pure acrylic acid present there. If necessary, the liquid pure acrylic acid from the reservoir can be conveyed via an external heat exchanger before it is returned to the transport and/or storage container.

The above-described method of transporting and/or of storing pure acrylic acid can be applied analogously to crude acrylic acid.

The invention is illustrated below by means of an illustrative embodiment.

A transport container having a capacity of 20 metric tons was filled with a freshly prepared pure acrylic acid of the following specification at 25° C.:

≧99.8% by weight of acrylic acid,
≦0.03% by weight of water,
200 ppm by weight of MEHQ,
≦1 ppm by weight of phenothiazine,
≦3 ppm by weight of aldehydes,
1300 ppm by weight of acetic acid and propionic acid and
250 ppm by weight of diacrylic acid.

EXAMPLE 1

An insulated transport container provided with cooling coils and having a capacity of 20 metric tons was filled with a freshly prepared acrylic acid which had a temperature of 21° C. and the following specification:

about 99.8% by weight of acrylic acid
320 ppm of water
200 ppm of MEHQ
<1 ppm of phenothiazine
<3 ppm of aldehydes
1280 ppm of acetic acid and propionic acid
150 ppm of diacrylic acid The transport container was cooled by means of a 1:1 mixture of glycol/water (−20° C.) for 6 hours, resulting in solidification of about half of the acrylic acid. After 5 days at an external temperature of 15–30° C. (night/day temperature), the temperature of the acrylic acid was about 13° C. and was still partly frozen. The diacrylic acid content was about 280 ppm.

The liquid part of the acrylic acid was pumped into a stock tank in which about 100 metric tons of acrylic acid at 21° C. were present, and part of this acrylic acid was pumped back into the transport container to melt the remaining frozen acrylic acid. The stock tank was provided with a pumping facility and a heat exchanger. The pumped circulation was maintained for about 3 hours until the transport container had been completely emptied.

EXAMPLE 2

The procedure of Example 1 was repeated, but the liquid part of the acrylic acid from the transport container was not pumped into a stock tank, but instead pumped from the transport container, conveyed through a heat exchanger maintained at 25° C. by means of warm water and returned to the transport container. In this embodiment too, the pumped circulation was maintained for about 3 hours until the transport container had been completely emptied.

We claim:

1. A method of transporting and/or storing a stabilized pure acrylic acid in a storage and/or transport container, which comprises ensuring that the stabilized pure acrylic acid is partly crystalline during the entire duration of transport and/or storage in the storage and/or transport container.

2. A method as claimed in claim 1, wherein the stabilized pure acrylic acid is introduced in the liquid state into the transport and/or storage container and a proportion of from 10 to 99%, based on the total amount of pure acrylic acid present in the transport and/or storage container, is subsequently frozen.

3. A method as claimed in claim 1, wherein the stabilized pure acrylic acid is introduced in the liquid state into the transport and/or storage container and a proportion of from 20 to 70%, based on the total amount of pure acrylic acid present in the transport and/or storage container, is subsequently frozen.

4. A method as claimed in claim 2 or 3, wherein the transport and/or storage container is provided with at least one heat exchanger and the pure acrylic acid is frozen by introducing a cooling medium into the heat exchanger.

5. A method as claimed in claim 1, wherein the transport and/or storage container is provided with at least one heat exchanger and the acrylic acid in the transport and/or storage container is completely melted by introducing a heating medium into the heat exchanger for the purposes of emptying the transport and/or storage container.

6. A method as claimed in claim 5, wherein a heat exchanger with which the transport and/or storage container is provided is a double wall.

7. A method as claimed in claim 5 or 6, wherein the temperature of the heating medium is <40° C.

8. A method as claimed in claim 1 or 5, wherein, for the purposes of emptying the transport and/or storage container, liquid acrylic acid is taken from the transport and/or storage container, heated to a temperature in the range from 15 to 40° C. in a heat exchanger located outside the transport and/or storage container and subsequently recirculated to the transport and/or storage container until the entire contents of the transport and/or storage container have been completely melted.

9. A method as claimed in claim 1 or 5, wherein, for the purposes of emptying the transport and/or storage container, liquid acrylic acid is taken from the transport and/or storage container, heated to a temperature in the range from 17 to 25° C. in a heat exchanger located outside the transport and/or storage container and subsequently recirculated to the transport and/or storage container until the entire contents of the transport and/or storage container have been completely melted.

10. A method as claimed in claim 8, wherein the liquid pure acrylic acid is taken off via a tube which dips into the liquid pure acrylic acid in the transport and/or storage container and has lateral perforations which are smaller than the internal diameter of the tube.

11. A method as claimed in claim 8, wherein the heated liquid acrylic acid is returned to the transport and/or storage container via a spray device.

12. A method as claimed in claim 8, wherein the liquid pure acrylic acid taken from the transport and/or storage container is conveyed into a thermostatted reservoir and subsequently recirculated to the transport and/or storage container.

13. A method as claimed in claim 12, wherein the liquid acrylic acid taken from the reservoir is conveyed via an external heat exchanger before it is returned to the transport and/or storage container.

14. A method as claimed in claim 9, wherein the liquid pure acrylic acid is taken off via a tube which dips into the liquid pure acrylic acid in the transport and/or storage container and has lateral perforations which are smaller than the internal diameter of the tube.

15. A method as claimed in claim 9, wherein the heated liquid acrylic acid is returned to the transport and/or storage container via a spray device.

16. A method as claimed in claim 9, wherein the liquid pure acrylic acid taken from the transport and/or storage container is conveyed into a thermostatted reservoir and subsequently recirculated to the transport and/or storage container.

17. A method as claimed in claim 15, wherein the liquid acrylic acid taken from the reservoir is conveyed via an external heat exchanger before it is returned to the transport and/or storage container.

18. A method as claimed in claim 13, wherein the heated liquid acrylic acid is returned to the transport and/or storage container via a spray device.

19. A method as claimed in claim 17, wherein the liquid pure acrylic acid taken from the transport and/or storage container is conveyed into a thermostatted reservoir and subsequently recirculated to the transport and/or storage container.

20. A method as claimed in claim 1, wherein the storage and/or transport time in the container is at least 1 day and is $\leq 6$ months.

* * * * *